United States Patent
Neumann et al.

(10) Patent No.: US 6,828,465 B2
(45) Date of Patent: Dec. 7, 2004

(54) METHOD FOR PRODUCING BISPHENOLS

(75) Inventors: Rainer Neumann, Krefeld (DE); Rolf Lanze, Krefeld (DE); Frieder Heydenreich, Düsseldorf (DE); Michael Bödiger, League City, TX (US); Michael Prein, Brasschaat (BE)

(73) Assignee: Bayer Aktiengesellschaft, Leverkusen (DE)

( * ) Notice: Subject to any disclaimer, the term of this patent is extended or adjusted under 35 U.S.C. 154(b) by 80 days.

(21) Appl. No.: 10/239,544

(22) PCT Filed: Mar. 14, 2001

(86) PCT No.: PCT/EP01/02845

§ 371 (c)(1),
(2), (4) Date: Dec. 16, 2002

(87) PCT Pub. No.: WO01/72677

PCT Pub. Date: Oct. 4, 2001

(65) Prior Publication Data

US 2004/0030195 A1 Feb. 12, 2004

(30) Foreign Application Priority Data

Mar. 27, 2000 (DE) .......................................... 100 15 014

(51) Int. Cl.$^7$ ................................................ C07C 37/68
(52) U.S. Cl. ..................................... 568/724; 568/728
(58) Field of Search ................................ 568/724, 728

(56) References Cited

U.S. PATENT DOCUMENTS

| | | | |
|---|---|---|---|
| 2,775,620 A | 12/1956 | Williamson | 260/619 |
| 4,859,803 A | 8/1989 | Shaw | 568/727 |
| 5,545,764 A * | 8/1996 | Berg et al. | 568/724 |

FOREIGN PATENT DOCUMENTS

EP     0 671 377     9/1995

* cited by examiner

Primary Examiner—Michael L. Shippen
(74) Attorney, Agent, or Firm—Joseph C. Gil; James R. Franks; John E. Mrozinski

(57) ABSTRACT

The present invention provides crystals of an adduct of a bisphenol and a phenol and methods of producing those crystals. The crystals may find use in preparing bisphenols.

9 Claims, 1 Drawing Sheet

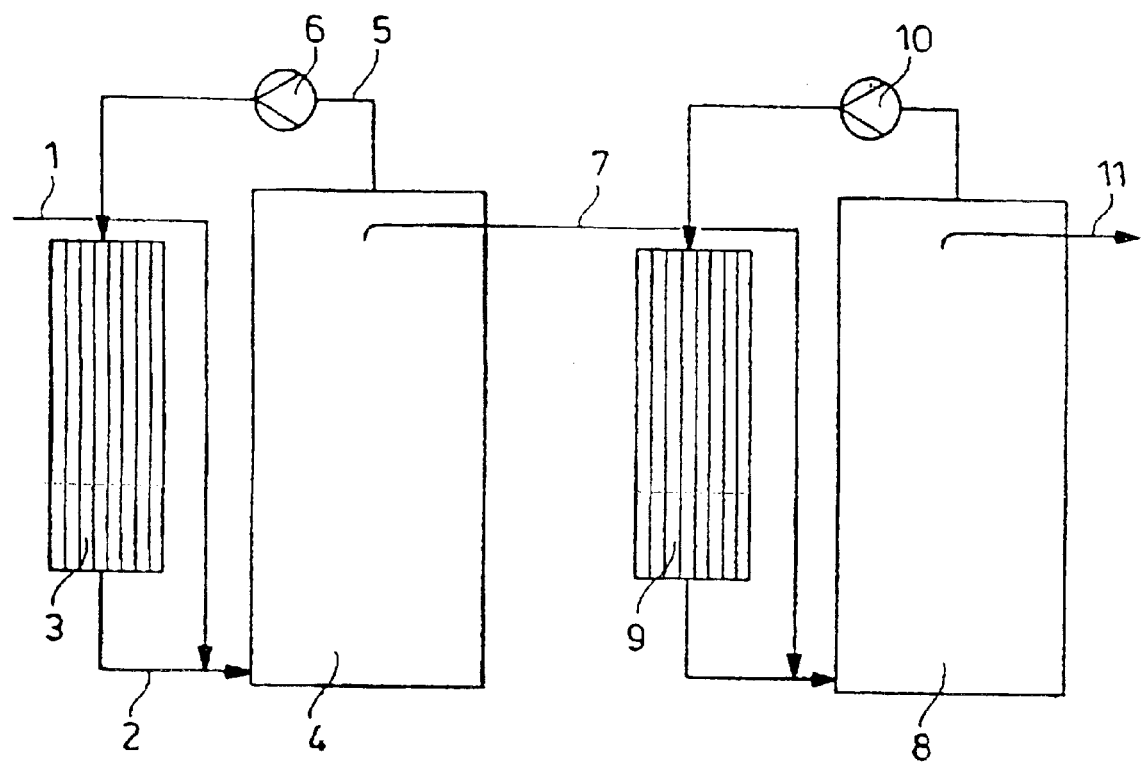

METHOD FOR PRODUCING BISPHENOLS

FIELD OF THE INVENTION

The present invention provides crystals of an adduct of a bisphenol and phenol, a process for preparing these crystals and a process for preparing bisphenols.

BACKGROUND OF THE INVENTION

Bis(4-hydroxyaryl)alkanes, in the following called bisphenols, are important as starting materials or as intermediates for preparing a number of commercial products. Bisphenols can be prepared by the condensation of phenols and carbonyl compounds. Substituted phenols or unsubstituted phenol may be used.

The condensation product from the reaction between phenol and acetone, 2,2-bis(4 hydroxyphenyl)propane (bisphenol A, BPA,) is of particular industrial importance. BPA is used as a starting material for preparing various types of polymer materials such as, for example, polyarylates, polyetherimides, polysulfones and modified phenol/formaldehyde resins. Preferred areas of application are the preparation of epoxy resins and polycarbonates.

Processes for preparing bisphenols by acid-catalysed reaction of phenols with carbonyl compounds are known, for example from U.S. Pat. No. 2,775,620 and from EP-A-0 342 758.

Bisphenols of general structure can be prepared by processes which are analogous to the preparation of BPA.

Bisphenols can be prepared via an adduct of bisphenol and phenol as an intermediate stage.

DETAILED DESCRIPTION OF THE INVENTION

The present invention is based on the object of providing an improved process, as compared with the prior art, of preparing bisphenols. The process according to the invention is intended to provide in particular bisphenol of high purity.

This object is achieved by a process for preparing crystals of an adduct of a bisphenol and a phenol comprising
a) the preparation of a solution containing bisphenol and phenol and
b) continuous performance of the crystallisation in one or more crystallisation devices which contain a crystallisation tank, a circulating pump and a cooler,
wherein the residence time of the liquid being crystallised in the crystallisation tank is 2 to 12 hours and
wherein crystallisation is performed in 1 to 5 stages, each consisting of the crystallisation devices mentioned and
wherein the temperature in the crystallisation tank in the last crystallisation stage is 40 to 70° C. and
wherein the concentration of bisphenol in the inflow to the first crystallisation stage is 15 to 40 wt. % and wherein, in the outflow from the last crystallisation stage, the concentration of bisphenol in dissolved form in the mother liquor is 10 to 20 wt. % and the proportion of crystallised solids in crystals of the adduct of a bisphenol and a phenol is 20 to 30 wt. %.

Accordingly, the present invention provides this process.

Furthermore, the object according to the invention is achieved by a process for preparing a bisphenol comprising preparing the adduct of a bisphenol and a phenol by the process according to the invention and obtaining the bisphenol from the adduct of the bisphenol and the phenol.

Accordingly, the present invention also provides this process.

Furthermore, the present invention provides crystals of the adduct of a bisphenol and a phenol obtainable by the process according to the present invention.

The process according to the invention is performed in such a way that the temperature in the crystallisation tank in the last crystallisation stage is 40 to 70° C., preferably 40 to 50° C., in particular 40 to 43° C.

The process according to the invention is performed in such a way that the concentration of bisphenol in the inflow to the first crystallisation stage is 15 to 40 wt. %, preferably 15 to 35 wt. %, in particular 25 to 35 wt. %.

As a result of the process according to the invention for preparing crystals of adducts of bisphenols and phenols, these crystals are obtainable in a form and a purity which has not been disclosed in the prior art.

The process according to the invention for preparing crystals of adducts of bisphenols and phenols has many advantages. Crystals are obtained which produce a bisphenol of such high quality that, after filtration and removal of the phenol, it can be used without further purification to produce high quality secondary products, for example polycarbonates, epoxide resins, formaldehyde resins, etc.

The process according to the invention for preparing crystals of adducts of bisphenols and phenols, and thus the process according to the invention for preparing bisphenols, also has the following advantage. It provides adducts of bisphenols and phenols and the bisphenol in such high purity that the further purification steps which are usually required to prepare a bisphenol suitable for high quality polycarbonates can be avoided. The mentioned further purification steps which are usually required are, for example, additional crystallisation steps or additional distillation steps.

Crystals of an adduct of a bisphenol and a phenol according to the invention have many advantages. They are readily filterable and have high purity. They have a low concentration of included impurities. Therefore the adduct of a bisphenol and a phenol is obtained in high purity following separation of the crystals by filtration.

If the bisphenol is recovered from the crystals of an adduct of a bisphenol and a phenol according to the invention, then this provides a novel, advantageous process for preparing bisphenols.

The present invention has many advantages. The process according to the invention is simple and thus cost-effective. Additional purification steps are not required. The products according to the invention are characterised by high quality, which is expressed by a low colour index, a high storage stability and a high thermal stability.

Any bisphenols at all may be used according to the invention. The preferred bisphenol according to the invention is bisphenol A.

Any phenols at all may be used according to the invention. The preferred phenol according to the invention is unsubstituted phenol.

The process according to the invention for preparing crystals of the adduct of a bisphenol and a phenol is preferably performed in one to five steps, particularly preferably one to three steps and very particularly preferably two steps. In the first step, temperatures of preferably less than 100° C., preferably less than 70° C. are used and in the last step, temperatures of preferably less than 70° C., particularly preferably less than 50° C., very particularly preferably less than 43° C. are used.

In the process according to the invention for preparing crystals of the adduct of a bisphenol and a phenol, a circulating crystallisation process preferably takes place. Each crystalliser step is preferably operated at 20 to 40 times, particularly preferably 25 to 35 times, in particular 30 times the rate of circulation, with respect to the throughput. According to the invention, a crystalliser step is understood to be a crystallisation device which contains a crystallisation tank, a circulating pump and a cooler. The rate of circulation is defined as the amount conveyed through the circulating pump per unit of time divided by the total amount supplied for crystallisation per unit of time.

In the process according to the invention for preparing crystals of the adduct of a bisphenol and a phenol, the procedure is preferably such that the circulating stream in the crystalliser is supplied tangentially at the foot of the crystalliser and is withdrawn centrally at the head of the crystalliser.

In the process according to the invention for preparing crystals of the adduct of a bisphenol and a phenol, the procedure is preferably such that the reaction mixture is cooled to temperatures below 80° C., particularly preferably to temperatures below 75° C., in particular 70° C., before crystallisation.

In the process according to the invention for preparing crystals of the adduct of a bisphenol and a phenol, the reaction mixture from which the adduct is crystallised is preferably mixed into the circulating stream directly upstream of the crystalliser.

In the process according to the invention for preparing crystals of the adduct of a bisphenol and a phenol, the procedure is such that the speed of flow up the crystalliser tank is 0.5 to 4, particularly preferably 2 to 3, very particularly preferably about 3 m per minute. The speed of flow upwards is the average speed of the liquid in the crystallisation tank, moving from bottom to top.

In the process according to the invention for preparing crystals of the adduct of a bisphenol and a phenol, the crystallisation tanks are preferably operated so that they are full of liquid.

In the process according to the invention for preparing crystals of the adduct of a bisphenol and a phenol, a circulating pump is preferably located above the crystallisation tank.

In the process according to the invention for preparing crystals of the adduct of a bisphenol and a phenol, the suspension of reaction mixture and adduct crystals contained therein is preferably circulated with a specific pump energy of at most 150 Watts/m$^3$, particularly preferably at most 100 Watts/m$^3$.

In the process according to the invention for preparing crystals of the adduct of a bisphenol and a phenol, the suspension preferably passes through the circulation cooler from top to bottom with a speed of preferably 1 to 5 m/sec, particularly preferably 2 to 4 m/sec, very particularly preferably 2.8 to 3.2 m/sec.

In the process according to the invention for preparing crystals of the adduct of a bisphenol and a phenol, the circulation cooler preferably contains electropolished tubes, in which the suspension is circulated. The surfaces of these electropolished tubes which are in contact with the suspension have a roughness which is preferably less than 1.5 $\mu$m, particularly preferably less than 1 $\mu$m. This has the advantage that long operating times are achieved for the circulation cooler, because only small amounts of deposit are formed on the surfaces.

In the process according to the invention for preparing crystals of the adduct of a bisphenol and a phenol, the circulation cooler is preferably operated with constant temperature warm water as a cooling medium. In this case, it is particularly preferable that the temperature difference between the constant temperature warm water and the suspension being cooled is 2 to 6 K, very particularly preferably 3 to 4 K.

In the process according to the invention for preparing crystals of the adduct of a bisphenol and a phenol, coatings are preferably removed from the internal surfaces of the suspension-carrying tubes in the circulation cooler at regular intervals of preferably 40 days by rapid heating to about 80° C. These coatings may consist, for example, of bisphenol and of the adduct of a bisphenol and a phenol.

In the process according to the invention for preparing crystals of the adduct of a bisphenol and a phenol, the crystalliser and the associated peripheral equipment is preferably cleaned at regular intervals of preferably 40 to 300 days by heating to preferably 80° C., wherein the circulation circuit continues to operate.

The preferred process according to the invention for preparing crystals of an adduct of a bisphenol and a phenol is suspension crystallisation in which the crystals of the adduct of a bisphenol and a phenol are obtained by cooling the reaction mixture.

The process according to the invention for preparing BPA is preferably based on the acid-catalysed reaction of phenol with acetone, wherein a ratio by amounts of phenol:acetone of greater than 5:1 is preferably used in the reaction. Homogeneous or heterogeneous Brönsted acids or Lewis acids are used as acid catalysts, that is, for example, strong mineral acids such as hydrochloric acid or sulfuric acid. Gel-like or macroporous sulfonated cross-linked polystyrene resins (acid ion exchangers) are preferably used. The details given below refer to a process of preparation using acid ion exchangers as catalysts.

In order to produce high selectivity, the reaction of phenol with acetone can be performed in the presence of suitable mercapto compounds as cocatalysts. These may either be dissolved homogeneously in the reaction solution or be fixed to the sulfonated polystyrene matrix via ionic or covalent bonds. The reaction unit is preferably a fixed layer bed or a fluidised bed which is traversed upwards or downwards or a column of the reactive distillation column type.

During the reaction of phenol with acetone in the presence of acid catalysts and mercapto compounds as cocatalysts, a product mixture is produced which contains, in addition to unreacted phenol and optionally acetone, primarily BPA and water. In addition, there are also small amounts of typical secondary products of the condensation reaction such as, for example, 2-(4-hydroxyphenyl)-2-(2-hydroxyphenyl) propane (o,p-BPA), substituted indenes, hydroxyphenyl indanoles, hydroxyphenyl chromanes, substituted xanthenes and higher condensed compounds with three or more phenyl rings in the molecular structure.

The secondary products mentioned, such as also water, phenol and acetone, may impair the suitability of BPA for preparing polymers and are preferably separated by suitable methods. High specifications relating to purity are generally required for the raw material BPA, in particular when preparing polycarbonate.

The working up and purification of BPA is normally performed by means of a multistage cascade of suitable purification processes such as, for example, suspension crystallisation, melt crystallisation, distillation and desorption. In a preferred embodiment, BPA is isolated from the reaction mixture in the form of an approximately equimolar crystalline adduct with phenol by cooling the reaction mixture, when the BPA/phenol adduct crystallises out. The crystallisation process is preferably performed as a suspension crystallisation. Suspension crystallisation is understood to be crystallisation from a liquid due to cooling, wherein the crystals form a suspension with the liquid. The BPA/phenol adduct crystals are then separated from the liquid phase, using equipment suitable for solid/liquid separation such as a rotary filter or a centrifuge, and if required taken on for further purification. Thus, adduct crystals are obtained which typically have a purity greater than 99 wt. % of BPA, with respect to the secondary components, with a phenol content of about 40 wt. %. Impurities which adhere to the surface of the adduct crystals can be removed by washing with suitable solutions which typically contain one or more components from the group acetone, water, phenol, BPA and secondary components.

The stream of liquid (mother liquor) produced during solid/liquid separation contains phenol, BPA, water produced during reaction and unreacted acetone and is enriched in the secondary components typically produced during BPA preparation. In a preferred embodiment, this mother liquor is recycled to the reaction unit. In order to maintain the catalytic activity of the acid ion exchanger any water produced is preferably first removed by distillation, wherein any acetone still present is also optionally removed from the mother liquor. The dewatered reaction stream obtained in this way is preferably topped up with phenol and acetone and returned to the reaction unit. Alternatively, water and acetone may also be partly or entirely removed by distillation prior to performing suspension crystallisation of the BPA/phenol adduct. During the distillation steps described above, some of the phenol present in the reaction solution may also be removed by distillation.

In the case of this type of circulation procedure the problem is that secondary products from the preparation of BPA accumulate in the circulation stream and can lead to deactivation of the catalyst system. In order to avoid excessive accumulation of secondary components in the circulation stream, some of the circulation stream, optionally after partial or complete recovery of phenol by distillation, is preferably excluded from the process chain as a BPA resin.

In addition, it has proven advantageous to pass some or the entire amount of the circulation stream, after solid/liquid separation and before or after the removal of water and residual acetone, over a rearrangement unit filled with acid ion exchanger. This unit is generally operated at a higher temperature than the reaction unit. In this rearrangement unit, under the conditions present therein, some of the secondary components from BPA preparation and present in the circulation stream are isomerised to give BPA, so that the overall yield of BPA can be increased.

The BPA/phenol adduct crystals obtained after the completion of suspension crystallisation of the reaction solution and solid/liquid separation as described above are then taken, if required, to further purification stages, wherein the removal of most of the phenol is achieved.

Thus, the adduct crystals can be recrystallised, for example, from phenol, from organic solvents, from water or from mixtures of the compounds mentioned in accordance with a suspension crystallisation procedure. The phenol present in the adduct crystals can also be entirely or partly removed by choosing a suitable solvent. The phenol optionally remaining in the BPA after recrystallisation can then be entirely removed by suitable distillation, desorption or extraction procedures.

Alternatively, phenol can also be removed first from the adduct crystals. Preferred methods for this are desorption of the melt using hot inert gases, vacuum distillation or a combination of the methods mentioned. In this way, it is possible to obtain BPA with a residual phenol concentration of less than 100 ppm from the adduct crystals. By means of suitable reaction management and optionally the addition of stabilisers, it can be ensured that BPA does not decompose to a marked extent under the thermal stresses experienced during the removal of phenol by distillation or desorption.

Depending on the process conditions for suspension crystallisation from the reaction solution and when performing the solid/liquid separation and crystal washing, the BPA obtained is suitable for preparing polymer materials after the removal of phenol from the adduct crystals. It may be necessary to take the BPA obtained after the removal of phenol to a further purification operation, in particular in order to prepare high quality materials such as polycarbonates. Final purification may be performed by suspension crystallisation from water or suitable organic solvents, melt crystallisation in the form of a static or dynamic layer crystallisation, extraction with water, aqueous neutral, acid or basic salt solutions or suitable organic solvents or in the form of a single-stage or multi-stage distillation. It is possible to obtain BPA with a purity of greater than 99.5 wt. % by performing the purification operations mentioned, or a suitable combination thereof, this BPA being particularly suitable for preparing high quality polymer materials.

In the following, a preferred embodiment of the invention is explained using a diagram (FIG. 1). The invention is not restricted to this preferred embodiment.

FIG. 1 shows a two step device for preparing crystals of adducts of bisphenol and phenol. Supplying the reaction mixture which contains bisphenol and phenol to the device is achieved via pipe 1. This opens into pipe 2 which supplies the circulating stream from heat exchanger 3 to the first crystallisation tank 4. The suspension is thus supplied tangentially at the foot of the crystallisation tank. The suspension of reaction mixture and crystals of the adduct of bisphenol and phenol is withdrawn laterally at the head of the crystallisation tank, through pipe 5, and supplied to heat exchanger 3 via circulating pump 6. The suspension is taken from the first crystallisation tank via pipe 7 and supplied to the second crystallisation step consisting of a second crystallisation tank 8, a second heat exchanger 9 and a second circulation pump 10. Finally, the suspension is taken out of the second crystallisation tank 8 via pipe 11 for further working up.

In the following, the invention is explained by means of an example, without being restricted to this.

EXAMPLE 1

According to the Invention

In order to work up and purify BPA, the reaction mixture from the preparation of BPA was supplied to suspension crystallisation equipment in accordance with FIG. 1. For this purpose, a 2 step crystallisation was performed, starting at 56° C. in the 1st step and then at 41° C. in the 2nd step, wherein the bisphenol content of the reaction solution being crystallised was 30%. The reaction mixture at about 70° C. was mixed into the circulating stream directly upstream of the crystallisation tank and an upwards speed of flow of about 3 m/min was maintained in the crystallisation tank.

Circulation crystallisation was operated at 30 times the rate of circulation (with respect to throughput) per crystalliser step and the circulating stream was supplied tangentially at the foot of the crystallisation tank and withdrawn centrally at the head of the crystallisation tank.

The circulation coolers were supplied from top to bottom at a speed of 3 m/s through electropolished tubes (advantage: long operating times for the crystalliser/circulation cooler due to the presence of only small amounts of deposit on the cooling surfaces) (surface roughness 1 μm) and the cooler was operated with constant temperature warm water. The maximum temperature difference from the product side was 3 to 4 K.

The circulation pump was located above the crystallisation tank upstream of the circulation cooler and was operated with a specific pump energy of at most 100 Watts/m$^3$ of suspension.

The final mixed crystal suspension was withdrawn laterally at the head of the crystallisation tank after a total residence time of 4 hours.

In order to remove BPA and BPA/phenol coatings, the internal surfaces of the cooling tubes were cleaned at regular intervals by rapidly heating up to 80° C. and the entire crystalliser system was cleaned at regular intervals by heating up the product contents and continuing to operate the circulation circuit.

Bisphenol A/phenol adduct crystals of high purity can be obtained by this type of crystallisation.

After filtration and separation of the phenol, bisphenol A with a purity of 99.5% and a colour index of 20 Haze was obtained. The Haze colour index was determined visually by comparing with APHA standard colorimetry solutions. The value is the number of mg of platinum [as potassium hexachloroplatinate(IV) with cobalt(II) chloride hexahydrate in a ratio of 1.246:1 dissolved in 1000 ml of aqueous hydrochloric acid] which has the same colour as the sample, with the same layer thickness.

The bisphenol A produced in this way can be reacted by a conventional process to give high purity polycarbonate. A 14% strength aqueous solution of sodium bisphenolate was prepared from the bisphenol A sample obtained in example 1 (purity >99.5%, colour index 20 Haze) by adding sodium hydroxide (6.5% in water) with the exclusion of oxygen. This solution was reacted with phosgene and phenol in the phase interface process. After working up, a polycarbonate with a relative solution viscosity of 1.297 was obtained. The YI (yellowness index) of the polycarbonate was 2.3, the light transmission (ASTM D 1003) was 87.88.

The yellowness index YI was measured in accordance with ASTM D 1925, the transmission in accordance with ASTM D 1003. The relative solution viscosity was determined at 25° C. using a solution containing 5 g of polymer per liter in dichloromethane.

EXAMPLE 2

Comparison Example

In order to work up and purify BPA, the reaction mixture from the preparation of BPA was supplied to suspension crystallisation equipment in accordance with FIG. 1. For this purpose, a 2 step crystallisation was performed, starting at 56° C. in the 1st step and then at 41° C. in the 2nd step, wherein the bisphenol content of the reaction solution being crystallised was 30%. The reaction mixture at about 70° C. was mixed into the circulating stream directly upstream of the crystallisation tank and an upwards speed of flow of about 3 m/min was maintained in the crystallisation tank.

Circulation crystallisation was operated at 5 times the rate of circulation (with respect to throughput) per crystalliser step and the circulating stream was supplied tangentially at the foot of the crystallisation tank and withdrawn centrally at the head of the crystallisation tank.

The circulation coolers were supplied from top to bottom at a speed of 0.5 m/s through non-electropolished tubes and the cooler was operated with constant temperature warm water. The maximum temperature difference from the product side was 3 to 4 K.

The circulation pump was located above the crystallisation tank upstream of the circulation cooler and was operated with a specific pump energy of at most 50 Watts/m$^3$ of suspension.

The final mixed crystal suspension was withdrawn laterally at the head of the crystallisation tank after a total residence time of 4 hours.

In order to remove BPA and BPA/phenol coatings, the internal surfaces of the cooling tubes had to be cleaned at short intervals by rapidly heating up to 80° C. and the entire crystalliser system had to be cleaned at short intervals (1×week) by heating up the product contents and continuing to operate the circulation circuit.

After filtration and separation of the phenol from the bisphenol A/phenol adduct crystals obtained in this way, bisphenol A with a purity of 99.3% and a colour index of 50 Haze was obtained. The bisphenol A obtained in this way cannot be processed by conventional processes to give extremely pure polycarbonate.

A 14% strength aqueous solution of sodium bisphenolate was prepared from the bisphenol A sample obtained in comparison example 2 (purity 99.3%, colour index 50 Haze) by adding sodium hydroxide (6.5% in water) with the exclusion of oxygen. This solution was reacted with phosgene and phenol in the phase interface process. After working up, a polycarbonate with a relative solution viscosity of 1.297 was obtained. The YI (yellowness index) of the polycarbonate was 3.1, the light transmission (ASTM D 1003) was 87.36%.

The YI was determined in the same way as described in example 1.

The foregoing examples of the present invention are offered for the purpose of illustration and not limitation. It will be apparent to those skilled in the art that the embodiments described herein may be modified or revised in various ways without departing from the spirit and scope of the invention. The scope of the invention is to be measured by the appended claims.

What is claimed is:

1. A process for preparing crystals of an adduct of a bisphenol and a phenol comprising:
   (a) preparing a solution containing bisphenol and phenol; and
   (b) crystallizing continuously said adduct of bisphenol and phenol in one or more crystallization devices which comprise a crystallization tank, a circulating pump and a cooler;

wherein, the residence time of the liquid being crystallized in the crystallization tank is 2 to 12 hours;

crystallization is performed in 1 to 5 stages, each of said stages containing the one or more crystallization devices;

the temperature in the crystallization tank in the last crystallization stage is 40 to 70° C.;

the concentration of bisphenol in the inflow to the first crystallization stage is 15 to 40 wt. %;

in the outflow from the last crystallization stage the concentration of bisphenol in dissolved form in the mother liquor is 10 to 20 wt. % and the proportion of crystallized solids in crystals of the adduct of a bisphenol and a phenol is 20 to 30 wt. %;

a suspension of crystals of said adduct of bisphenol and phenol is circulated through each crystallization tank at a specific pump energy of at most 150 Watts/m$^3$, and said suspension of crystals of said adduct of bisphenol and phenol is circulated through said cooler having a top and a bottom at a speed of 1 m/s to 5 m/s from said top of said cooler to said bottom of said cooler.

2. The process according to claim 1, wherein the bisphenol is bisphenol A and wherein the phenol is an unsubstituted phenol.

3. The crystals of the adduct of a bisphenol and a phenol made by the process according to claim 1.

4. The crystals of the adduct of bisphenol A and unsubstituted phenol made by the process according to claim 2.

5. The process for preparing a bisphenol according to claim 1 further comprising recovering the bisphenol from the adduct of the bisphenol and the phenol.

6. The process for preparing bisphenol A according to claim 2 further comprising recovering the bisphenol A from the adduct of bisphenol A and phenol.

7. The process of claim 1 wherein said suspension of crystals of said adduct of bisphenol and phenol is circulated through each crystallization tank at a specific pump energy of at most 100 Watts/m$^3$, and said suspension of crystals of said adduct of bisphenol and phenol is circulated through said cooler at a speed of 2 m/s to 4 m/s from said top of said cooler to said bottom of said cooler.

8. The process of claim 1 wherein said suspension of crystals of said adduct of bisphenol and phenol is circulated through said cooler at a speed of 2.8 m/s to 3.2 m/s from said top of said cooler to said bottom of said cooler.

9. The process of claim 1 wherein the liquid being crystallized is circulated through each crystallization tank at a circulation rate, and the liquid being crystallized passes through each crystallization tank at a throughput rate, and the ratio of said circulation rate to said throughput rate is 30.

* * * * *